United States Patent [19]
Nakahara et al.

[11] Patent Number: 5,374,366
[45] Date of Patent: Dec. 20, 1994

[54] SYNTHETIC LUBRICATING OIL

[75] Inventors: Makoto Nakahara, Osaka; Katsuhiro Fujii, Kobe; Masao Izumi, Suita, all of Japan

[73] Assignee: Sanken Chemical Co., Ltd., Osaka, Japan

[21] Appl. No.: 19,304

[22] Filed: Feb. 18, 1993

[30] Foreign Application Priority Data

Apr. 15, 1992 [JP] Japan .................. 4-121149
Apr. 15, 1992 [JP] Japan .................. 4-121150

[51] Int. Cl.$^5$ .................. C10M 105/42; C07C 69/67
[52] U.S. Cl. .................. 252/56 D; 252/56 R; 252/56 S; 252/68; 252/79; 560/185; 554/213
[58] Field of Search .............. 252/56 R, 56 S, 52 A, 252/56 D, 58, 67, 68, 73, 79; 560/185; 554/213; C10M 105/42

[56] References Cited

U.S. PATENT DOCUMENTS

| | | | |
|---|---|---|---|
| 2,158,107 | 5/1939 | Carruthers | 560/185 |
| 3,759,862 | 9/1973 | Fukui et al. | 560/185 |
| 4,292,187 | 9/1981 | Hentschel et al. | 252/56 S |
| 5,021,179 | 6/1991 | Zehler et al. | 252/56 S |
| 5,096,606 | 3/1992 | Hagihara et al. | 252/56 S |

FOREIGN PATENT DOCUMENTS 3-128991 5/1991 Japan .
3-128992 5/1991 Japan .
WO90/12849 11/1990 WIPO .
WO91/07479 5/1991 WIPO .

OTHER PUBLICATIONS

*Polymer Preprints,* Japan, vol. 41, No. 11 (1992), pp. 4703-4705, Katsuhiro Fujii et al., "The Molecular Structure of the ester-oligomers and its Compatibility with the Alternative of a Specific Chlorofluorocarbons"*, Sep. 10, 1992.

*Polymer Preprints,* Japan (English Edition), vol. 41, Nos. 5-11, p. E1681, Katsuhiro Fujii et al., "The Molecular Structure of the ester-oligomers and its Compatibility with the Alternative of a Specific Chlorofluorocarbons"**, Sep. 10, 1992.

*Primary Examiner*—Prince Willis, Jr.
*Assistant Examiner*—Alan D. Diamond
*Attorney, Agent, or Firm*—Stevens, Davis, Miller & Mosher

[57] ABSTRACT

A synthetic lubricating oil contains an esterification product obtained from a hydroxycarboxylic acid polyol ester (A) and at least one aliphatic monocarboxylic acid (B), and optionally either an aliphatic carboxylic acid having two or more carboxyl groups (C) or a combination of an aliphatic carboxylic acid having two or more carboxyl groups (C) and an aliphatic polyhydric alcohol (D).

28 Claims, No Drawings

SYNTHETIC LUBRICATING OIL

The present invention relates to a synthetic ester lubricating oil with high viscosity index, low pour point and improved resistances to heat, weather and hydrolysis. Particularly, it relates to a refrigerating machine oil having high miscibility with hydrogen-containing fluoroalkane refrigerants.

Because the use conditions of lubricating oils have become severe due to the rapid developments of various industries in recent years, the lubricating oils have been required to have not only good lubricating oil characteristics such as high viscosity and low pour point but also high thermal stability. Therefore, mineral oils, which have been conventionally used for this purpose, have become unsatisfactory with respect to such performance characteristics. Instead of mineral oils, ester synthetic oils have come to be used. However, they disadvantageously tend to suffer from reduction of acid value or change in viscosity due to the oxidation, hydrolysis, etc., and have not been satisfactory enough as, in particular, lubricating oils used at very high temperatures, such as in turbo-supercharged-engine oils. On the other hand, to refrigerating machine oils are required not only high thermal stability but also good miscibility with refrigerants. Conventional lubricating oils are unsatisfactory with respect to both miscibility and thermal stability, particularly when they are used as a lubricating oil in an atmosphere of a hydrogen-containing fluoroalkane refrigerant.

Under the circumstances as mentioned above, an object of the present invention is to provide a synthetic lubricating oil which has not only good lubricating oil characteristics but also high resistances to heat, weather and hydrolysis. In particular, it is to provide a refrigerating machine oil having high miscibility with hydrogen-containing fluoroalkane refrigerants in a wide temperature range.

The present inventor conducted various researches in order to achieve the above object, and consequently found that a specified ester compound can achieve the above object, whereby the present invention has been accomplished.

According to the present invention, there are provided a synthetic lubricating oil which comprises an esterification product obtained from a hydroxycarboxylic acid polyol ester (A) and at least one aliphatic monocarboxylic acid (B), and optionally either an aliphatic carboxylic acid having two or more carboxyl groups (C) or a combination of an aliphatic carboxylic acid having two or more carboxyl groups (C) and an aliphatic polyhydric alcohol (D); and a synthetic lubricating oil which comprises a compound of the formula,

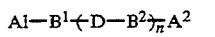  (I)

wherein
n is an integer between 0 and 4;
D is —OC—CO— or a residue having the formula,

—OC—R$^6$—CO—, in which R$^6$ is a C$_1$-C$_8$ linear or branched alkyl group;
B$^1$ and B$^2$ are independently a residue having the formula,

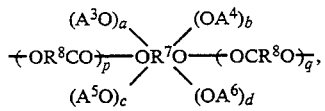

wherein a, b, c and d are independently 0 or 1;
p and q are independently 0, 1, 2 or 3;
R$^7$ is di-, tri-, tetra-, penta- or hexavalent C$_1$-C$_{12}$ linear or branched saturated hydrocarbon group which may contain —O— group;
R$^8$ is a C$_1$-C$_7$ linear or branched alkylene group; with the proviso that B$^1$ and B$^2$ do not simultaneously have the formula,

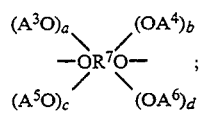

A$^1$, A$^2$, A$^3$, A$^4$, A$^5$ and A$^6$ are independently a residue having the formula,

R$^9$—CO—

R$^9$ is a C$_1$-C$_{11}$ linear or branched alkyl group.

In the above formulas, n is preferably 0 or 1; R$^8$ is preferably —C(CH$_3$)$_2$— or —CH$_2$—C(CH$_3$)$_2$—; A$^1$, A$^2$, A$^3$, A$^4$, A$^5$ and A$^6$ are preferably CH$_3$—, CH$_3$—(CH$_2$)$_4$—, CH$_3$—(CH$_2$)$_5$—, CH$_3$—(CH$_2$)$_6$—, CH$_3$—(CH$_2$)$_7$—, CH$_3$—CH$_2$—C(CH$_3$)$_2$—, CH$_3$—(CH$_2$)$_3$—CH(C$_2$H$_5$)— or CH$_3$—C(CH$_3$)$_2$—CH$_2$—CH(CH$_3$)—CH$_2$—; D is preferably —(CH$_2$)$_4$— or —(CH$_2$)$_2$—; and R$^7$ is preferably

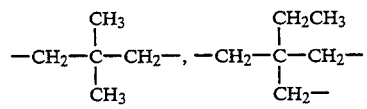

or

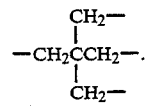

The synthetic lubricating oil of the present invention can be used for various purposes. For example, it can be used as an engine oil for automobiles, gear oil for automobiles, industrial gear oil, gear oil for rolling, etc. Since it is miscible particularly with hydrogen-containing fluoroalkane refrigerants in a wide temperature range, it can be used also as a refrigerating machine oil.

The compound of the formula (I) can be prepared by various processes.

For example, the compound can be obtained from a hydroxycarboxylic acid polyol ester (A) and at least one aliphatic monocarboxylic acid (B), and optionally either an aliphatic carboxylic acid having two or more carboxyl groups (C) or a combination of an aliphatic carboxylic acid having two or more carboxyl groups (C) and an aliphatic polyhydric alcohol (D).

The hydroxycarboxylic acid polyol ester (A) may be (i) a mono-, di- or polyester compound obtained by esterification of a hydroxycarboxylic acid and a polyhydroxy compound, or (ii) a monoester compound obtained by self-condensation of a hydroxyalkyl aldehyde.

The hydroxycarboxylic acid (hereinafter A1) is preferably a compound of the formula, $$HO-R^1-COOH$$

wherein $R^1$ is a $C_1-C_7$ linear or branched alkylene group.

Specific examples of the hydroxycarboxylic acid (A1) are glycolic acid, lactic acid, hydroxyisobutyric acid, hydroxypivalic acid, hydroxyoctanoic acid, etc.

Of these, $HO-C(CH_3)_2-COOH$ and $HO-CH_2-C(CH_3)_2-COOH$ are preferred.

Specific examples of the polyhydroxy compound are neopentyl glycol, 2,2-diethyl-1,3-propanediol, 2-butyl-2-ethyl-1,3-propanediol, trimethylolethane, trimethylolpropane, ditrimethylolpropane, pentaerythritol, dipentaerythritol, tripentaerythritol, ethylene glycol, diethylene glycol, polyethylene glycols, propylene glycol, dipropylene glycol, polypropylene glycols, 2-ethyl-1,3-hexanediol, glycerol, diglycerol, polyglycerols, 1,2,4-butanetriol, 1,2,6-hexanetriol, sorbitol, mannitol, etc.

Of these, trimethylol propane, neopentyl glycol and pentaerythritol are preferred.

The hydroxyalkyl aldehyde (hereinafter A3) is preferably a compound of the formula, $$HO-R^3-CHO$$

wherein $R^3$ is a $C_1-C_4$ linear or branched alkylene group.

Specific examples of the hydroxyalkyl aldehyde (A3) are glycolaldehyde, hydroxy-isobutylaldehyde, 4-hydroxy-3-methylbutylaldehyde, hydroxypivalaldehyde, etc.

Of these, $HO-CH_2-C(CH_3)_2-CHO$ is preferred.

The aliphatic monocarboxylic acid (B) is a compound of the formula, $$R^4-COOH$$

wherein $R^4$ is a $C_1-C_{11}$ linear or branched alkyl group.

Specific examples of the aliphatic monocarboxylic acid (B) are acetic acid, propionic acid, butyric acid, isobutyric acid, valeric acid, isovaleric acid, pivalic acid, caproic acid, 2-methylvaleric acid, 3-methylvaleric acid, 4-methylvaleric acid, 2,2-dimethylbutyric acid, 2-ethylbutyric acid, tertbutylbutyric acid, enanthic acid, 2,2-dimethylpentanoic acid, 2-ethylpentanoic acid, 3-ethylpentanoic acid, 2-methylhexanoic acid, 4-methylhexanoic acid, 5-methylhexanoic acid, caprylic acid, 2-ethylhexanoic acid, 3,5-dimethylhexanoic acid, 2,2-dimethylhexanoic acid, 2-methylheptanoic acid, 3-methylheptanoic acid, 4-methylheptanoic acid, 2-propylpentanoic acid, pelargonic acid, 2,2-dimethylheptanoic acid, 3,5,5-trimethylhexanoic acid, 2-methyloctanoic acid, 2-ethyloctanoic acid, 2-ethylheptanoic acid, 3-methyloctanoic acid, capric acid, undecanoic acid, and lauric acid. Lower alkyl esters and acid anhydrides of these compounds, etc. can also be used.

Of these, preferred are compounds having the formula, $$R^4-COOH$$

wherein $R^4$ is $CH_3-$, $CH_3-(CH_2)_4-$, $CH_3-(CH_2)_5-$, $CH_3-(CH_2)_6-$, $CH_3-(CH_2)_7-$, $CH_3-CH_2-C(CH_3)_2-$, $CH_3-(CH_2)_3-CH(C_2H_5)-$ or $CH_3-C(CH_3)_2-CH_2-CH(CH_3)-CH_2-$.

The aliphatic polycarboxylic acid having two or more carboxyl groups (C) is preferably oxalic acid or an dicarboxylic acid having the formula, $$HOOC-R^5-COOH$$

wherein $R^5$ is a $C_1-C_8$ linear or branched alkylene group.

Specific examples of the aliphatic carboxylic acid having two or more carboxyl groups (C) are oxalic acid, malonic acid, methylmalonic acid, succinic acid, ethylmalonic acid, dimethylmalonic acid, methylsuccinic acid, glutaric acid, adipic acid, 2,2-dimethylsuccinic acid, 2,2,3-trimethylsuccinic acid, 2-methylglutaric acid, butylmalonic acid, diethylmalonic acid, 2,2-dimethylglutaric acid, 2,4-dimethylglutaric acid, 3,3-dimethylglutaric acid, 2-ethyl-2-methylsuccinic acid, 3-methyladipic acid, pimelic acid, suberic acid, 2,2-dimethyladipic acid, azelaic acid, and sebacic acid. Lower alkyl esters and acid anhydrides of these compounds, etc. can also be used.

Of these, succinic acid and adipic acid are preferred.

The aliphatic polyhydric alcohol (D) is preferably a compound selected from the group consisting of: neopentyl glycol, 2,2-diethyl-1,3-propanediol, 2-butyl-2-ethyl-1,3-propanediol, trimethylolethane, trimethylolpropane, ditrimethylolpropane, pentaerythritol, dipentaerythritol, tripentaerythritol, ethylene glycol, diethylene glycol, polyethylene glycols, propylene glycol, dipropylene glycol, polypropylene glycols, 2-ethyl-1,3-hexanediol, glycerol, diglycerol, polyglycerols, 1,2,4-butanetriol, 1,2,6-hexanetriol, sorbitol, and mannitol.

Of these, neopentyl glycol and trimethylol propane are preferred.

In any of the cases where (A)+(B), (A)+(B)+(C) or (A)+(B)+(C)+(D) are reacted, the reaction of the starting materials are usually carried out with controlling the molar ratio of the carboxyl groups contained in the materials to the hydroxyl groups contained in the materials within the range of from 0.9 to 1.2. After the reaction had been completed, the excess alcohols and acids are removed by an after-treatment such as alkali cleaning, water washing, adsorption, etc. Preferably, the reaction and after-treatment are conducted so that the treated ester compound has an acid value of not more than 5 and a number of hydroxyl groups per molecule of not more than 20.

In the present invention, the esterification product may be produced by either a one-stage process in which all the starting materials are reacted at the same time, or a two-stage process in which the aliphatic monocarboxylic acid alone is reacted later. The esterification is carried out by a conventional method while eliminating reaction by-products such as water from the system. This reaction is carried out, for example, at a reaction temperature of 100°-250° C. in the presence or absence of a catalyst and optionally in the presence of a solvent such as toluene, xylene or the like.

Since the esterification product is used as a component of the synthetic lubricating oil of the present invention, the esterification product usually has a kinematic viscosity determined at 40° C. falling within the range of from 5 to 1,000 cSt, preferably of from 15 to 460 cSt. It usually has a pour point of not higher than −10° C., preferably not higher than −25° C. When the kinematic viscosity is lower than 5 cSt, the lubricating property of the synthetic lubricating oil is sometimes inferior. When, to the contrary, it is higher than 1,000 cSt, the handling and operation of the synthetic lubricating oil are sometimes inferior. When the pour point is higher than −10° C., the oil sometimes freezes in a refrigerator or the like whereby the function as a lubricating oil is lost.

The synthetic lubricating oil of the present invention comprises the thus obtained ester as main constituent. Depending on the purpose of use, it may contain mineral oils or synthetic oils (e.g. poly-α-olefins, alkylbenzenes, esters other than the aforementioned ester, polyethers, perfluoropolyethers and phosphoric esters), etc. If necessary, there can be added additives for lubricating oil such as phenol antioxidants (e.g. 2,4-dibutyl-4-methylphenol), antihydrolysis agents such as epoxy compounds (e.g. carboxylic acid glycidyl esters and glycidyl ethers), extreme pressure agents, oiliness improvers, antifoaming agents, metal deactivators, etc.

The Synthetic lubricating oil of the present invention can be used as a refrigerating machine oil in an atmosphere of a hydrogen-containing fluoroalkane refrigerant, Specific examples of the hydrogen-containing fluoroalkane are tetrafluoroalkane (e.g. 1,1,1,2-tetrafluoroethane (HFC-134a) and 1,1,2,2-tetrafluoroethane (HFC-134)), pentafluoroalkane (e.g. 1,1,1,2,2-pentafluoroethane (HFC-125)), trifluoroalkane (e.g. 1,1,2-trifluoroethane (HFC-143), 1,1,1-trifluoroethane (HFC-143a) and trifluoromethane (HFC-23)) difluoroalkane (e.g. 1,1-difluoroethane (HFC-152a) and difluoromethane (HFC-32)), fluoromethane, and the mixtures of these.

The synthetic lubricating oil of the present invention is excellent not only in lubricating oil characteristics such as viscosity index and pour point but also in thermal resistance, weather resistance and hydrolysis resistance. Hence, it is excellent as a lubricating oil used under severe conditions. Furthermore, it has a good miscibility with hydrogen-containing fluoroalkane refrigerants and hence is excellent also as a refrigerating machine oil.

The present invention is illustrated with reference to the following examples. However, it should not be interpreted that the present invention is limited to the scope.

EXAMPLE 1

Into a four-necked flask equipped with a stirrer, a nitrogen inlet tube, a thermometer and a separator provided with a cooling coil was charged 300 g of powdered hydroxypivalaldehyde. It was melted by heating. Tetrakisacetylacetonatozirconium was added thereto as a catalyst in an amount of 0.03% based on the amount of hydroxypivalaldehyde. The reaction was terminated by rapid cooling when the temperature dropped from 148° C. to 130° C. The product thus obtained was distilled at 140°–153° C. under a vacuum of 3–6 mmHg to obtain 285 g of hydroxypivalic acid neopentyl glycol monoester. To 204 g (1 mole) of this monoester were added 116 g (1 mole) of caproic acid, 158 g (1 mole) of pelargonic acid and 0.9 g of dibutyltin oxide as a catalyst. Thereafter, the resulting mixture was heated at 220° C. to carry out esterification while eliminating the produced water from the system until a theoretical amount of water was produced. After completion of the reaction, the reaction mixture was washed with a 5% aqueous sodium hydroxide solution and then with water, dehydrated, and then treated with clay to obtain reaction product A.

The reaction product A was a mixture of the compounds of the formula:

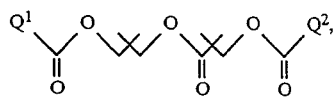

wherein $Q^1$ and $Q^2$ are independently

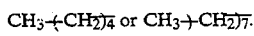

$CH_3\text{-}(CH_2)_4$ or $CH_3\text{-}(CH_2)_7$.

EXAMPLE 2

To 204 g (1 mole) of hydroxypivalic acid neopentyl glycol monoester prepared in the same manner as in Example 1 were added 158 g (2 moles) of 3,5,5-trimethylhexanoic acid and 0.9 g of dibutyltin oxide as a catalyst. The resulting mixture was subjected to reaction and purification in the same manner as in Example 1 to obtain a reaction product B.

The reaction product B was a compound of the formula:

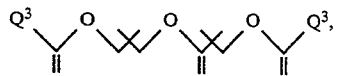

wherein $Q^3$ is $(CH_3)_3CCH_2CH(CH_3)CH_2$—.

EXAMPLE 3

Into the same reactor as used in Example 1 were charged 134 g (1 mole) of trimethylolpropane, 118 g (1 mole) of hydroxypivalic acid and 0.9 g of tetrabutoxytitanium as a catalyst. The resulting mixture was heated at 180° C. Esterification was carried out while eliminating the produced water from the system until a theoretical amount of water was produced. Thus, hydroxypivalic acid trimethylolpropane ester was obtained. To this ester were added 260 g (2 moles) of enanthic acid and 130 g (1 mole) of 2,2-dimethylbutanoic acid. The resulting mixture was subjected to reaction and purification in the same manner as in Example 1 to obtain a reaction product C.

The reaction product C was a mixture of the compounds of the formula:

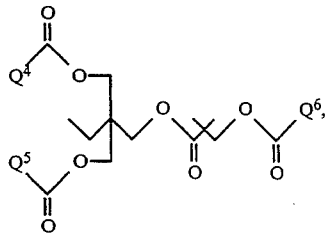

wherein $Q^4$, $Q^5$ and $Q^6$ are independently

$CH_3\text{-}(CH_2)_5$ or $CH_3CH_2C(CH_3)_2$—.

EXAMPLE 4

Into the same reactor as used in Example 1 were charged 104 g (1 mole) of neopentyl glycol, 236 g (2 moles) of hydroxypivalic acid and 0.9 g of dibutyltin oxide as a catalyst. The resulting mixture was heated at 180° C. Esterification was carried out while eliminating the produced water from the system until a theoretical amount of water was produced. Thus, hydroxypivalic acid neopentyl glycol ester was obtained. To this ester was added 260 g (2 moles) of enanthic acid. The resulting mixture was subjected to reaction and purification in the same manner as in Example 1 to obtain a reaction product D.

The reaction product D was a compound of the formula:

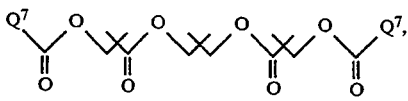

wherein $Q^7$ is $CH_3\text{---}(CH_2)_5$.

EXAMPLE 5

Into the same reactor as used in Example 1 were charged 104.1 g (1 mole) of hydroxyisobutyric acid, 136 g (1 mole) of pentaerythritol and 1.0 g of dibutyltin oxide as a catalyst. The resulting mixture was heated at 180° C. Esterification was carried out while eliminating the produced water from the system until a theoretical amount of water was produced. Thus, hydroxyisobutyric acid pentaerythritol ester was obtained. To this ester were added 288 g (2 moles) of 2-ethylhexanoic acid and 232 g (2 moles) of caproic acid. The resulting mixture was subjected to reaction and purification in the same manner as in Example 1 to obtain a reaction product E.

The reaction product E was a mixture of the compounds of the formula:

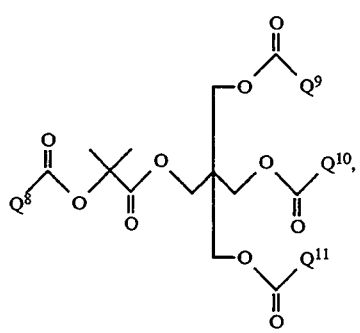

wherein $Q^8$, $Q^9$, $Q^{10}$ and $Q^{11}$ are independently $CH_3\text{---}(CH_2)_4$ or $CH_3\text{---}(CH_2)_3 CH(C_2H_5)\text{---}$.

EXAMPLE 6

Into the same reactor as used in Example 1 were charged 408 g (2 moles) of hydroxypivalic acid neopentyl glycol monoester prepared in the same manner as in Example 1, 14.6 g (0.1 mole) of adipic acid and 0.9 g of tetrabutoxytitanium as a catalyst. The resulting mixture was heated at 220° C. Esterification was carried out while eliminating the produced water from the system until a theoretical amount of water was produced. Then, 601 g (3.8 moles) of 3,5,5-trimethylhexanoic acid was added. The resulting mixture was subjected to reaction and purification in the same manner as in Example 1 to obtain a reaction product F.

The reaction product F was a mixture of the compound of the formula (1):

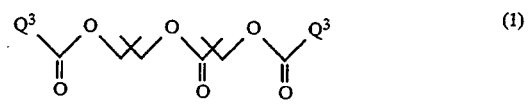 (1)

wherein $Q^3$ is as defined above, and the compounds of the formulas (2.1)–(2.3):

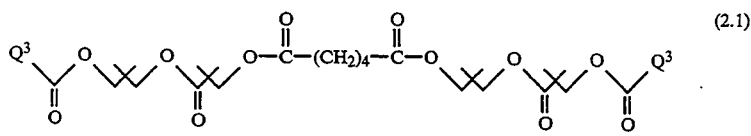 (2.1)

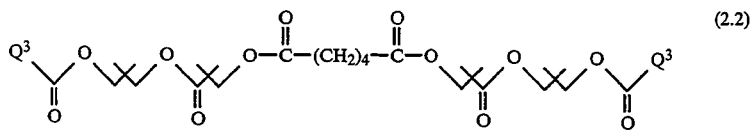 (2.2)

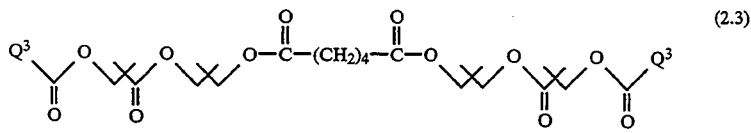 (2.3)

wherein $Q^3$ is as defined above.

The molar ratio of the compound of the formula (1) to the compounds of the formulas (2.1)–(2.3) was 0.9:0.1.

EXAMPLE 7

Reaction and purification were carried out in the same manner as in Example 6 except for changing the amounts of adipic acid and 3,5,5-trimethylhexanoic acid to 73 g (0.5 mole) and 475 g (3 moles), respectively. Thus, a reaction product G was obtained.

The reaction product G was a mixture of the compound of the above formula (1) and the compounds of the above formulas (2.1)–(2.3), in which the molar ratio of the compound of the formula (1) to the compounds of the formulas (2.1)–(2.3) was 2:1.

EXAMPLE 8

Reaction and purification were carried out in the same manner as in Example 6 except for changing the amounts of adipic acid and 3,5,5-trimethylhexanoic acid to 146 g (1 mole) and 316.5 g (2 moles), respectively. Thus, a reaction product H was obtained.

The reaction product H was a mixture of the compounds of the above formulas (2.1)–(2.3).

EXAMPLE 9

Reaction and purification were carried out in the same manner as in Example 6 except for changing the amounts of adipic acid to 146 g (1 mole) and using 260.4 g (2 moles) of enanthic acid in place of 3,5,5-trimethylhexanoic acid. Thus, a reaction product I was obtained.

The reaction product I was a mixture of the compounds of the formulas (3.1)–(3.3).

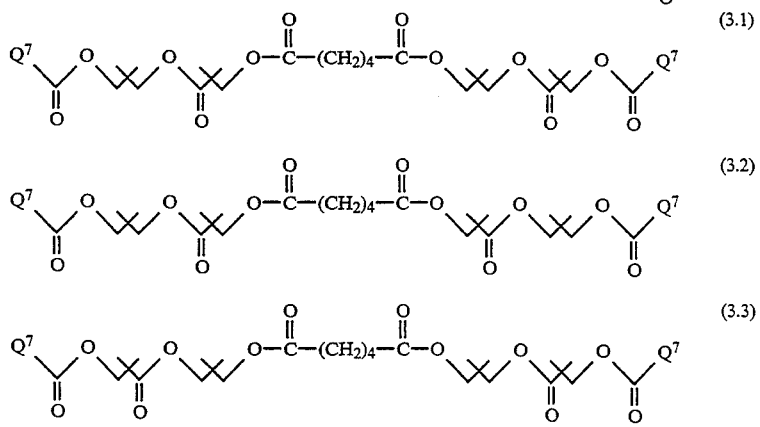

wherein $Q^7$ is as defined above.

EXAMPLE 10

Into the same reactor as used in Example 1 were charged 204 g (1 mole) of hydroxypivalic acid neopentyl glycol monoester prepared in the same manner as in Example 1, 118 g (1 mole) of succinic acid, 104 g (1 mole) of neopentyl glycol, 144 g (1 mole) of 2-ethylhexanoic acid, 116 g (1 mole) of caproic acid and 0.9 g of tetrabutoxytitanium as a catalyst. The resulting mixture was subjected to reaction and purification in the same manner as in Example 1 to obtain a reaction product J.

The reaction product J was a mixture of the compounds of the formulas (4.1) and (4.2):

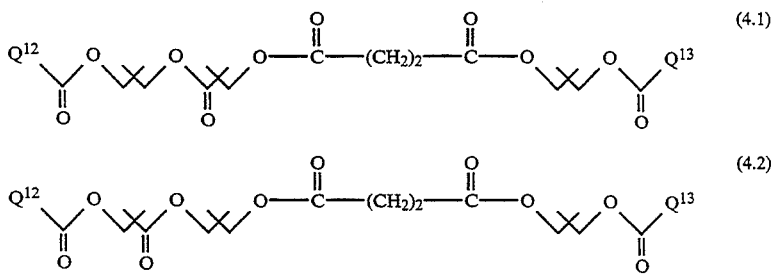

wherein $Q^{12}$ and $Q^{13}$ are independently $CH_3\text{-}(CH_2)_4\text{-}$ or $CH_3\text{-}(CH_2)_3 CH(C_2H_5)\text{-}$.

EXAMPLE 11

Into the same reactor as used in Example 1 were charged 166.6 g (1.6 moles) of hydroxyisobutyric acid, 104 g (1.6 moles) of neopentyl glycol and 0.2 g of dibutyltin oxide as a catalyst. The resulting mixture was heated at 220° C. Esterification was carried out while eliminating the produced water from the system until a theoretical amount of water was produced. Thus, hydroxyisobutyric acid neopentyl glycol monoester was obtained. To this monoester were added 146 g (1 mole) of adipic acid, 173 g (1.2 moles) of caprylic acid and 0.7 g of dibutyltin oxide, and the resulting mixture was subjected to reaction and purification in the same manner as in Example 1 to obtain reaction product K.

The reaction product K was a mixture of the compounds of the formula:

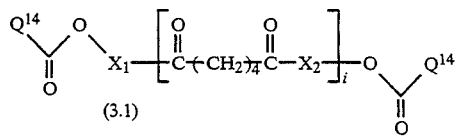

wherein $X_1$ and $X_2$ are independently $-CH_2C(CH_3)_2COOCH_2C(CH_3)_2CH_2-$ or $-CH_2C(CH_3)_2C-H_2OOCC(CH_3)_2CH_2-$; $Q^{14}$ is $CH_3\text{-}(CH_2)_6$; and i is a number of repetition of the bracketed unit and has an average value of 1.7.

EXAMPLE 12

Into the same reactor as used in Example 1 were charged 354 g (3 moles) of hydroxypivalic acid, 208 g (2 moles) of neopentyl glycol and 0.3 g of dibutyltin oxide as a catalyst. The resulting mixture was heated at 220° C. Esterification was carried out while eliminating the produced water from the system until a theoretical amount of water was produced. Thus, hydroxypivalic acid neopentyl glycol ester was obtained. To this ester were added 146 g (1 mole) of adipic acid, 60.5 (1 mole) of acetic acid, 144 g (1 mole) of caprylic acid and 0.7 g of dibutyltin oxide. The resulting mixture was subjected to reaction and purification in the same manner as in Example 1 to obtain a reaction product L.

The reaction product L was a mixture of the compounds of the formula:

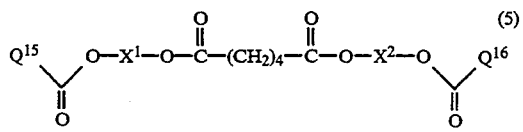 (5)

wherein Q$^{15}$ and Q$^{16}$ are independently

CH$_3$-(CH$_2$)$_6$ or CH$_3$—;
and X$^1$ and X$^2$ are independently
—CH$_2$C(CH$_3$)$_2$COOCH$_2$C(CH$_3$)$_2$CH$_2$—,
—CH$_2$C(CH$_3$)$_2$CH$_2$OOCC(CH$_3$)$_2$CH$_2$—, or
—CH$_2$C(CH$_3$)$_2$COOCH$_2$C(CH$_3$)$_2$CH$_2$OOCC(CH$_3$)$_2$CH$_2$—.

EXAMPLE 13

Into the same reactor as used in Example 1 were charged 118 g (1 mole) of hydroxypivalic acid, 134 g (1 mole) of trimethylolpropane and 0.2 g of dibutyltin oxide as a catalyst. The resulting mixture was heated at 220° C. Esterification was carried out while eliminating the produced water from the system until a theoretical amount of water was produced. Thus, hydroxypivalic acid trimethylolpropane monoester was obtained. To this monoester were added 146 g (1 mole) of adipic acid, 104 g (1 mole) of neopentyl glycol, 432.6 g (3 moles) of caprylic acid and 0.7 g of dibutyltin oxide. The resulting mixture was subjected to reaction and purification in the same manner as in Example 1 to obtain a reaction product M.

The reaction product M was a compound of the formula:

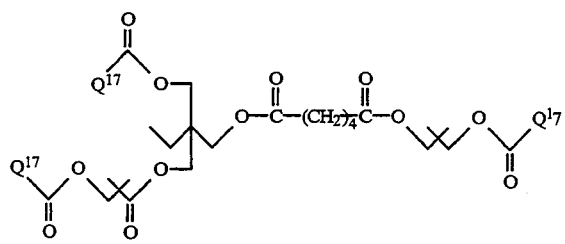

wherein Q$^{17}$ is CH$_3$-(CH$_2$)$_6$.

Comparative Example 1

Into the same reactor as used in Example 1 were charged 152 g (2 moles) of propylene glycol, 146 g (1 mole) of adipic acid and 400 g (2 moles) of lauric acid. The resulting mixture was allowed to react with one another in the same manner as in Example 1 to obtain an esterification product N.

The esterification product N was a compound of the formula:

$$CH_3\text{-}(CH_2)_{10}\text{-}\overset{O}{\underset{\|}{C}}\text{-}O\text{-}CH_2\overset{CH_3}{\underset{|}{CH}}\text{-}O\text{-}\overset{O}{\underset{\|}{C}}\text{-}(CH_2)_4\overset{O}{\underset{\|}{C}}\text{-}O\text{-}\overset{CH_3}{\underset{|}{CH}}CH_2O\overset{O}{\underset{\|}{C}}\text{-}(CH_2)_{10}\text{-}CH_3.$$

Comparative Example 2

In the same manner as in Comparative Example 1, 136 g (1 mole) of pentaerythritol was reacted with 520 g (4 moles) of enanthic acid to obtain pentaerythritol tetraenathate O.

The reaction product O was a compound of the formula:

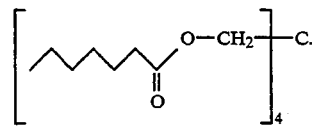

Comparative Example 3

In the same manner as in Comparative Example 1, 146 g (1 mole) of adipic acid was reacted with 260 g (2 moles) of 2-ethylhexanol to obtain dioctyl adipate P.

The reaction product P was a compound of the formula:

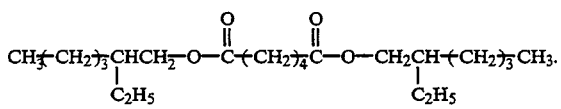

Table 1 shows physical property of the compounds of the above examples and comparative examples. Table 2 shows the results of tests of thermal stability, chemical stability, hydrolysis resistance and miscibility with the refrigerant HFC 134a. These properties were determined evaluated by the following methods.

Thermal stability test:

In a 100-ml sample bottle was placed 60 g of a test oil. The acid value and the kinematic viscosity ratio (40° C.) after a test at 140° C. for 168 hours were measured.

Chemical stability (sealed tube) test:

In a glass tube were placed 10 g of a test oil and 5 g of HFC 134a, and rods of 3 mm in diameter and 27 mm in length of copper, iron and aluminum, respectively, were added as catalysts. Then, the glass tube was sealed up and the color tone and the change of the catalysts after a test at 175° C. for 14 days were observed.

Hydrolysis resistance test:

In a glass tube were placed 30 g of a test oil and 1,000 ppm of water, and rods of 3 mm in diameter and 27 mm in length of copper, iron and aluminum, respectively, were added as catalysts. The inner atmosphere of the glass tube was replaced by nitrogen. Thereafter, the glass tube was sealed up. The color tone, the acid value and the change of the catalysts after a test at 175° C. for 14 days were observed.

Test of miscibility with refrigerant:

HFC 134a and a test oil were placed in a glass tube so as to adjust the proportion of the oil to 10%. Thereafter, the glass tube was sealed up. The temperature at separation into two layers in the range of −60° C. to +100° C. was measured.

TABLE 1

| | Compound | Kinematic viscosity (cSt) 40° C. | Kinematic viscosity (cSt) 100° C. | Viscosity index | Pour point (°C.) | Acid value (KOH mg/g) |
|---|---|---|---|---|---|---|
| Example | A | 13.2 | 3.53 | 152 | ←−50 | 0.01 |
| | B | 29.4 | 5.30 | 113 | ←−50 | 0.01 |
| | C | 33.4 | 6.02 | 126 | ←−50 | 0.01 |
| | D | 19.1 | 4.28 | 136 | −50 | 0.01 |
| | E | 61.6 | 9.63 | 138 | −45 | 0.01 |
| | F | 31.0 | 5.49 | 114 | −45 | 0.01 |
| | G | 58.7 | 8.37 | 113 | −45 | 0.01 |
| | H | 224 | 20.1 | 104 | −30 | 0.01 |
| | I | 68.0 | 9.92 | 130 | ←−50 | 0.01 |
| | J | 46.5 | 7.79 | 137 | ←−50 | 0.01 |
| | K | 186 | 21.2 | 138 | −45 | 0.01 |
| | L | 370 | 37.4 | 139 | −35 | 0.01 |
| | M | 112 | 15.3 | 144 | ←−55 | 0.01 |
| Comparative Example | N | 26.4 | 5.34 | 139 | −15 | 0.01 |
| | O | 21.4 | 4.70 | 139 | −40 | 0.01 |
| | P | 7.6 | 2.43 | 142 | ←−50 | 0.01 |

TABLE 2

| | Compound | Thermal stability test Acid value (KOH mg/g) | Thermal stability test Viscosity ratio (40° C.) | Chemical stability test Color tone (ASTM) | Chemical stability test State of catalyst | Hydrolysis resistance test Acid value (KOH mg/g) | Hydrolysis resistance test Color tone (ASTM) | Hydrolysis resistance test State of catalyst | Miscibility test High temp. range (°C.) | Miscibility test Low temp. range (°C.) |
|---|---|---|---|---|---|---|---|---|---|---|
| Example | A | 0.32 | 1.03 | L0.5 | Unchanged | 0.8 | L0.5 | Unchanged | >100 | ←−60 |
| | B | 0.03 | 1.00 | L0.5 | Unchanged | 0.4 | L0.5 | Unchanged | >100 | ←−60 |
| | C | 0.07 | 1.00 | L0.5 | Unchanged | 0.3 | L0.5 | Unchanged | >100 | −50 |
| | D | 0.40 | 1.04 | L0.5 | Unchanged | 0.7 | L0.5 | Unchanged | >100 | ←−60 |
| | E | 0.18 | 1.01 | L0.5 | Unchanged | 0.6 | L0.5 | Unchanged | >100 | −50 |
| | F | 0.03 | 1.00 | L0.5 | Unchanged | 0.4 | L0.5 | Unchanged | >100 | ←−60 |
| | G | 0.04 | 1.00 | L0.5 | Unchanged | 0.5 | L0.5 | Unchanged | >100 | ←−60 |
| | H | 0.06 | 1.00 | L0.5 | Unchanged | 0.7 | L0.5 | Unchanged | 80 | ←−60 |
| | I | 0.08 | 1.00 | L0.5 | Unchanged | 0.7 | L0.5 | Unchanged | >100 | ←−60 |
| | J | 0.07 | 1.01 | L0.5 | Unchanged | 0.8 | L0.5 | Unchanged | >100 | ←−60 |
| | K | 0.12 | 1.01 | L0.5 | Unchanged | 0.9 | 1 | Unchanged | 60 | ←−60 |
| | L | 0.10 | 1.02 | L0.5 | Unchanged | 1.4 | 1 | Unchanged | 70 | ←−60 |
| | M | 0.05 | 1.00 | L0.5 | Unchanged | 0.7 | L0.5 | Unchanged | >100 | ←−60 |
| Comparative Example | N | 1.35 | 1.03 | 3 | Iron was corroded | 5.4 | 4 | Iron was corroded | Separated | Separated |
| | O | 0.42 | 1.02 | L0.5 | Unchanged | 2.0 | 1 | Unchanged | Separated | Separated |
| | P | 1.50 | 1.02 | 2 | Unchanged | 3.6 | 4 | Iron was corroded | >100 | −50 |

What is claimed is:

1. A synthetic lubricating oil which comprises the esterification product of a hydroxycarboxylic acid polyol ester (A), at least one aliphatic monocarboxylic acid (B) and an aliphatic carboxylic acid having two or more carboxylic acid groups (C).

2. The synthetic lubricating oil of claim 1, wherein the esterification product has a kinematic viscosity determined at 40° C. falling within the range of from 5 to 1,000 cSt.

3. The synthetic lubricating oil of claim 1, wherein the hydroxycarboxylic acid polyol ester (A) is a hydroxycarboxylic acid alkylene glycol ester.

4. The synthetic lubricating oil of claim 3, wherein the hydroxycarboxylic acid alkylene glycol ester is a compound having the formula, $$HOCH_2C(CH_3)_2COOCH_2C(CH_3)_2CH_2OH.$$

5. The synthetic lubricating oil of claim 1, wherein the hydroxycarboxylic acid polyol ester (A) is (i) a mono-, di- or polyester compound obtained by esterification of a hydroxycarboxylic acid (A1) represented by the formula, $$HO-R^1-COOH$$

wherein $R^1$ is a $C_1$-$C_7$ linear or branched alkylene group, and a polyhydroxy compound (A2) selected from the group consisting of:

neopentyl glycol, 2,2-diethyl-1,3-propanediol, 2-butyl-2-ethyl-1,3-propanediol, trimethylolethane, trimethylolpropane, ditrimethylolpropane, pentaerythritol, dipentaerythritol, tripentaerythritol, ethylene glycol, diethylene glycol, polyethylene glycols, propylene glycol, dipropylene glycol, polypropylene glycols, 2-ethyl-1,3-hexanediol, glycerol, diglycerol, polyglycerols, 1,2,4-butanetriol, 1,2,6-hexanetriol, sorbitol and mannitol; or (ii) a monoester compound obtained by self-condensation of a hydroxyalkyl aldehyde (A3) represented by the formula, $$HO-R^3-CHO$$

wherein $R^3$ is a $C_1$-$C_4$ linear or branched alkylene group.

6. The synthetic lubricating oil of claim 5, wherein the hydroxycarboxylic acid polyol ester (A) is the mono-, di- or polyester compound (i).

7. The synthetic lubricating oil of claim 6, wherein the hydroxycarboxylic acid polyol ester (A) is a mono-, di- or polyester compound obtained by esterification of a hydroxycarboxylic acid (A1) selected from the group consisting of HO—C(CH$_3$)$_2$—COOH and HO—CH$_2$—C(CH$_3$)$_2$—COOH and a polyhydroxy compound (A2) selected from the group consisting of trimethylol propane, neopentyl glycol and pentaerythritol.

8. The synthetic lubricating oil of claim 5, wherein the hydroxycarboxylic acid polyol ester (A) is the monoester compound (ii).

9. The synthetic lubricating oil of claim 8, wherein the hydroxycarboxylic acid polyol ester (A) is a monoester compound obtained by-self-condensation of HO—CH$_2$—C(CH$_3$)$_2$—CHO.

10. The synthetic lubricating oil of claim 1, wherein the aliphatic monocarboxylic acid (B) is a compound represented by the formula,

R$^4$—COOH wherein R$^4$ is a C$_1$-C$_{11}$ linear or branched alkyl group.

11. The synthetic lubricating oil of claim 10, wherein the aliphatic monocarboxylic acid (B) is a compound represented by the formula,

R$^4$—COOH wherein R$^4$ is CH$_3$—, CH$_3$—(CH$_2$)$_4$—, CH$_3$—(CH$_2$)$_5$—, CH$_3$—(CH$_2$)$_6$—, CH$_3$—(CH$_2$)$_7$—, CH$_3$—CH$_2$—C(CH$_3$)$_2$—, CH$_3$—(CH$_2$)$_3$—CH(C$_2$H$_5$)— or CH$_3$—C(CH$_3$)$_2$—CH$_2$—CH(CH$_3$)—CH$_2$—.

12. The synthetic lubricating oil of claim 1, wherein the aliphatic carboxylic acid having two or more carboxyl groups (C) is oxalic acid or a dicarboxylic acid represented by the formula,

HOOC—R$^5$—COOH wherein R$^5$ is a C$_1$-C$_8$ linear or branched alkylene group.

13. The synthetic lubricating oil of claim 12, wherein the aliphatic carboxylic acid (C) is succinic acid or adipic acid.

14. A synthetic lubricating oil which comprises the esterification product of a hydroxycarboxylic acid polyol ester (A), at least one aliphatic monocarboxylic acid (B), an aliphatic carboxylic acid having two or more carboxyl groups (C) and an aliphatic polyhydric alcohol (D).

15. The synthetic lubricating oil of claim 14, wherein the aliphatic polyhydric alcohol (D) is a compound selected from the group consisting of:
neopentyl glycol, 2,2-diethyl-1,3-propanediol, 2-butyl-2-ethyl-1,3-propanediol, trimethylolethane, trimethylolpropane, ditrimethylolpropane, pentaerythritol, dipentaerythritol, tripentaerythritol, ethylene glycol, diethylene glycol, polyethylene glycols, propylene glycol, dipropylene glycol, polypropylene glycols, 2-ethyl-1,3-hexanediol, glycerol, diglycerol, polyglycerols, 1,2,4-butanetriol, 1,2,6-hexanetriol, sorbitol and mannitol.

16. The synthetic lubricating oil of claim 15, wherein the aliphatic polyhydric alcohol (D) is neopentyl glycol or trimethylol propane.

17. The synthetic lubricating oil of claim 14, wherein the esterification product has a kinematic viscosity determined at 40° C. falling within the range of from 5 to 1,000 cSt.

18. The synthetic lubricating oil of claim 14, wherein the hydroxycarboxylic acid polyol ester (A) is a hydroxycarboxylic acid alkylene glycol ester.

19. The synthetic lubricating oil of claim 18, wherein the hydroxycarboxylic acid alkylene glycol ester is a compound having the formula,

HOCH$_2$C(CH$_3$)$_2$COOCH$_2$C(CH$_3$)$_2$CH$_2$OH.

20. The synthetic lubricating oil of claim 14, wherein the hydroxycarboxylic acid polyol ester (A) is
(i) a mono-, di- or polyester compound obtained by esterification of a hydroxycarboxylic acid (A1) represented by the formula,

HO—R$^1$—COOH wherein R$^1$ is a C$_1$-C$_7$ linear or branched alkylene group, and a polyhydroxy compound (A2) selected from the group consisting of:
neopentyl glycol, 2,2-diethyl-1,3-propanediol, 2-butyl-2-ethyl-1,3-propanediol, trimethylolethane, trimethylolpropane, ditrimethylolpropane, pentaerythritol, dipentaerythritol, tripentaerythritol, ethylene glycol, diethylene glycol, polyethylene glycols, propylene glycol, dipropylene glycol, polypropylene glycols, 2-ethyl-1,3-hexanediol, glycerol, diglycerol, polyglycerols, 1,2,4-butanetriol, 1,2,6-hexanetriol, sorbitol and mannitol; or
(ii) a monoester compound obtained by self-condensation of a hydroxyalkyl aldehyde (A3) represented by the formula,

HO—R$^3$—CHO wherein R$^3$ is a C$_1$-C$_4$ linear or branched alkylene group.

21. The synthetic lubricating oil of claim 20, wherein the hydroxycarboxylic acid polyol ester (A) is the mono, di- or polyester compound (i).

22. The synthetic lubricating oil of claim 21, wherein the hydroxycarboxylic acid polyol ester (A) is a mono-, di- or polyester compound obtained by esterification of a hydroxycarboxylic acid (A1) selected from the group consisting of HO—C(CH$_3$)$_2$—COOH and HO—CH$_2$—C(CH$_3$)$_2$—COOH and a polyhydroxy compound (A2) selected from the group consisting of trimethylol propane, neopentyl glycol and pentaerythritol.

23. The synthetic lubricating oil of claim 20, wherein the hydroxycarboxylic acid polyol ester (A) is the monoester compound (ii).

24. The synthetic lubricating oil of claim 23, wherein the hydroxycarboxylic acid polyol ester (A) is a monoester compound obtained by self-condensation of HO—CH$_2$—C(CH$_3$)$_2$—CHO.

25. The synthetic lubricating oil of claim 14, wherein the aliphatic monocarboxylic acid (B) is a compound represented by the formula,

R$^4$—COOH wherein R$^4$ is a C$_1$-C$_{11}$ linear or branched alkyl group.

26. The synthetic lubricating oil of claim 25, wherein the aliphatic monocarboxylic acid (B) is a compound represented by the formula, $$R^4\text{—COOH}$$

wherein $R^4$ is $CH_3$—, $CH_3$—$(CH_2)_4$—, $CH_3$—$(CH_2)_5$—, $CH_3$—$(CH_2)_6$—, $CH_3$—$(CH_2)_7$—, $CH_3$—$CH_2$—$C(CH_3)_2$—, $CH_3$—$(CH_2)_3$—$CH(C_2H_5)$— or $CH_3$—$C(CH_3)_2$—$CH_2$—$CH(CH_3)$—$CH_2$—.

27. The synthetic lubricating oil of claim 14, wherein the aliphatic carboxylic acid having two or more carboxyl groups (C) is oxalic acid or a dicarboxylic acid represented by the formula, $$HOOC\text{—}R^5\text{—COOH}$$

wherein $R^5$ is a $C_1$-$C_8$ linear or branched alkylene group.

28. The synthetic lubricating oil of claim 27, wherein the aliphatic carboxylic acid (C) is succinic acid or adipic acid.

* * * * *